United States Patent [19]

Hynes et al.

[11] Patent Number: 4,487,838

[45] Date of Patent: Dec. 11, 1984

[54] RADIO-LABELLED CROSS-LINKING REAGENTS

[75] Inventors: Richard O. Hynes, Belmont; Martin A. Schwartz, Boston, both of Mass.

[73] Assignee: Massachusetts Institute of Technology, Cambridge, Mass.

[21] Appl. No.: 338,946

[22] Filed: Jan. 12, 1982

[51] Int. Cl.³ .................... G01N 33/58; C07C 117/00; G01N 21/75; G01N 33/60

[52] U.S. Cl. .................... 436/504; 548/542; 548/545; 260/349

[58] Field of Search .................... 436/504; 424/1.1; 252/301.1; 260/429.1, 349; 548/542, 545

[56] References Cited

U.S. PATENT DOCUMENTS 3,940,420 2/1976 Smith .................... 260/326.26

FOREIGN PATENT DOCUMENTS 2917001 11/1979 Fed. Rep. of Germany.

OTHER PUBLICATIONS

Dolly, J. O. et al., Biochemical Journal, vol. 193 (3), pp. 919–923 (1981).
Habeeb, A. F., Biochem. Biophys. Acta, vol. 673 (4), pp. 527–538.
Ji, T. H. et al., J. Biological Chemistry, vol. 255, pp. 2990–2993 (1980).
Dentler, W. L. et al., J. Cellular Biology, vol. 84, pp. 381–403.
Schwartz, M. A. et al., J. Biological Chem., vol. 257 (5), pp. 2343–2349, (3-10-1982).
Abdella, P. M. et al., B.B.R.C., vol. 87, No. 3, pp. 734–742, (4-13-1979).
Carlsson, J. et al., Biochem. J., vol. 173, pp. 723–737, (9-1-1978).
Chong, P. C. S. et al., J. Biol. Chem., vol. 256 (10), pp. 5064–5070, 5071–5076, (5-25-81).
Kitagawa, T. et al., Chemical and Pharmaceutical Bulletin, vol. 29 (4), pp. 1130–1135, (1981).
Friebel, K. et al., Hoppe-Seyler's Z. Physiol. Chem., vol. 362 (4), pp. 421–428, (4-1981).
Seela, Frank, Zeitsch fuer Naturforschung, vol. 31, (7–8), pp. 389–392, (1976).
Peters, K. et al., Annual Review Biochem., vol. 46, pp. 523–551, (1977), Academic Press.
Demoliou, C. D. et al., Biochemistry, vol. 19 (20), pp. 4539–4546, (9-30-1980).
Jaffe, C. L. et al., Biochemistry, vol. 19 (19), pp. 4423–4429, (9-16-1980).
Kiehm, D. J. et al., J. Biol. Chem., vol. 252 (23), pp. 8524–8531, (12-10-1977).
Lomant, A. J. et al., J. Molecular Biology, vol. 104 (1), pp. 243–261, (1976), Abstract.
Ngo, T. T. et al., J. Biol. Chem., vol. 256 (21), pp. 11313–11318, (11-10-1981).
Smith, R. J. et al., Biochemistry, vol. 17 (18), pp. 3719–3723, (9-5-1978).
Vanin, E. F. et al., Biochemistry, vol. 20 (24), pp. 6754–6760, (11-24-1981).
Zakowski, J. J. et al., J. Virology, vol. 36 (1), pp. 93–102, (10-1980).
Lewis, R. V. et al., Archives of Biochem. Biophys., vol. 190 (1), pp. 163–173, (9-1978).
Politz, S. M. et al., Biochemistry, vol. 20 (2), pp. 372–378, (1981).
Ji, J. Biological Chemistry, vol. 252 (5), pp. 1566–1570, (3-1977).

*Primary Examiner*—Benjamin R. Padgett
*Assistant Examiner*—M. Moskowitz
*Attorney, Agent, or Firm*—Arthur A. Smith, Jr.; Thomas J. Engellenner

[57] ABSTRACT

A crosslinking reagent consisting of a first functional group capable of forming a covalent derivative with a material of interest; a second functional group capable of forming an in situ bond to a neighboring material upon activation; a cleavable bond separating said first and second groups; and a radioactive marker to identify the neighboring material after cleavage of said bond, whereby in situ protein interactions can be studied.

11 Claims, 1 Drawing Figure

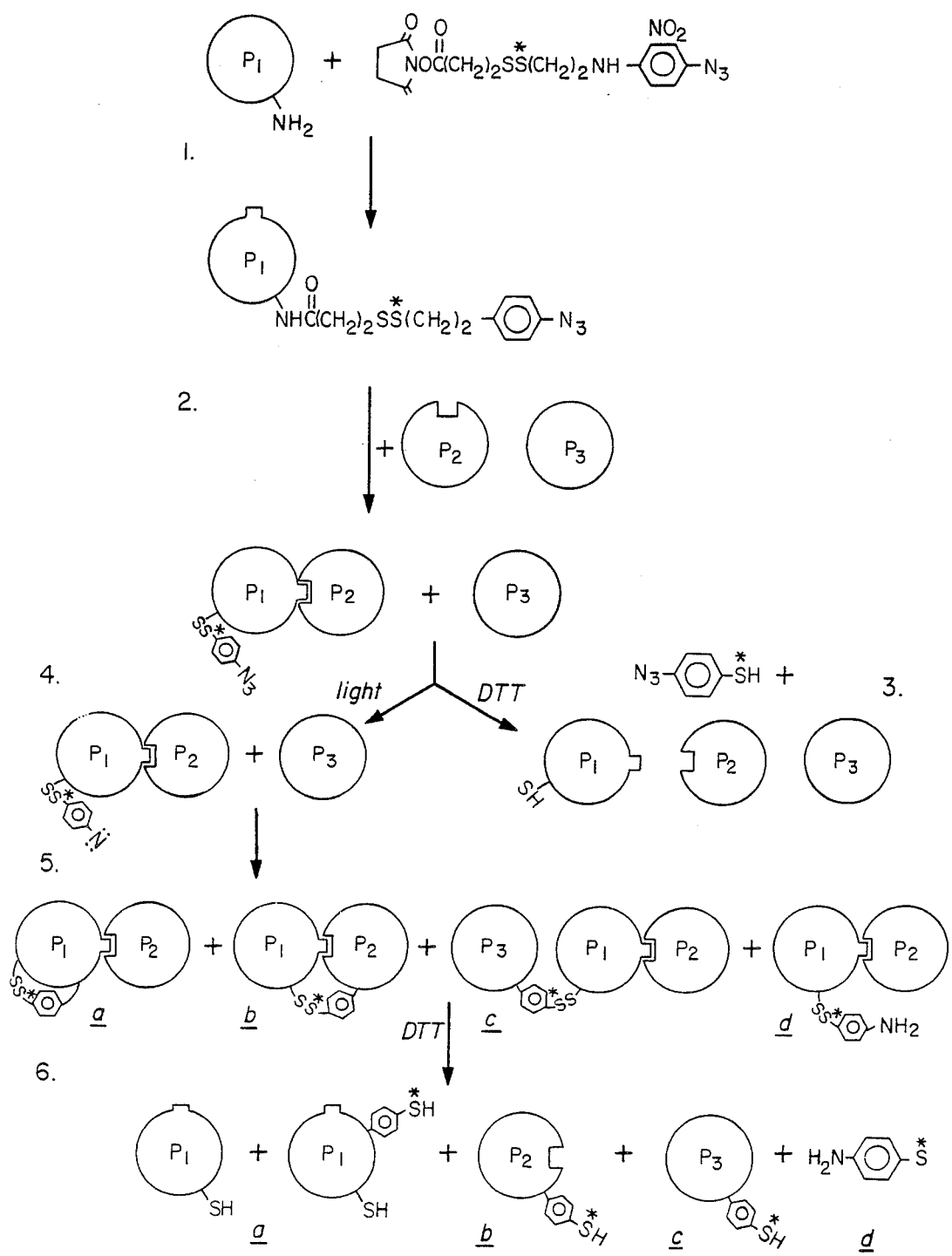

4,487,838

RADIO-LABELLED CROSS-LINKING REAGENTS

The Government has rights in this invention pursuant to Grant Number NIH-2-RO1-CA17007-06A1 awarded by the Department of Health and Human Services.

TECHNICAL FIELD

The field of this invention is biochemical analysis and, more particularly, chemical cross-linking reagents for studying protein interactions and the like.

BACKGROUND ART

The structures, organization and functions of cytoskeletal filaments, membranes, extracellular matrices and other biological systems depend on specific interactions between many macromolecules. A major problem which faces biologists is to identify these specific interactions. One approach is to isolate macromolecules and examine their interactions in vitro, but this approach is limited by the difficulty of extrapolating results to the situation in living cells. The in vitro approach needs to be supplemented with methods for analyzing protein-protein interactions in situ.

Attention is directed to an article by K. Peters and F. M. Richards entitled, "Chemical Cross-Linking: Reagents and Problems in Studies of Membrane Structure" in 46 *Annual Review of Biochemistry* 523–551 (1977) wherein the authors describe the state-of-the-art in studying protein-protein interactions in situ using chemical cross-linking reagents. Attention is also directed to an article by T. H. Ji entitled "A Novel Approach to the Identification of Surface Receptors" in 252 *Journal of Biological Chemistry* 1566–1570 (1977) and an article by D. J. Kiehm and T. H. Ji entitled "Photochemical Cross-Linking of Cell Membranes" in 252 *Journal of Biological Chemistry* 8524–8531 (1977), wherein a cleavable photosensitive cross-linking reagent is disclosed.

In general bifunctional cross-linking reagents serve to join a first material, i.e. a protein, with a second material, for example, an interacting protein. The cross-linked complexes are analyzed by gel electrophresis and this data leads to hypotheses on the interactions or proximity of such materials in biological systems. A major problem with this technique is the limitation of gel electrophoresis; large complexes formed by macromolecules can not be effectively taken up into the gels and electrophoretically distinguished.

Cleavable bifunctional crosslinkers, as described in the Peters article cited above, are also known. A cleavable crosslinker permits two-way electrophoresis. The complexes are first subjected to electric field induced migration in one direction and then reduced to cleave the crosslinker and subjected to migration in a second, typically perpendicular, direction. This cleaving technique is also limited since the complexity of the patterns often precludes meaningful conclusions.

Heterobifunctional crosslinkers are designed for two-stage crosslinking where a material of interest, for example a hormone, can be isolated, linked to one end of the reagent and then introduced in situ for reaction at the other end. This technique typically involves the use of photosensitive crosslinkers; a protein, with one end of the crosslinker attached thereto, is introduced into the system and the other end of the crosslinker is unreactive until it is photolyzed. Analysis by electrophoresis is simplified because one component of the complex is known: the introduced protein.

Related to crosslinking reagents are affinity probes. In such probes, a radioactively-labelled molecule or protein is attached to a reagent and introduced into the biological system. Complexes formed by the probe can be identified by their radioactivity and analyzed by electrophoresis.

There exists a need for better cross-linking reagents, particularly cleavable heterobifunctional cross-linkers. Moreover, it would be advantageous to have a cross-linking reagent that can donate an identifiable label which will remain on the second material or protein after cleavage. This "donation" property would permit the complexes formed by the crosslinker to be reduced to their constituent parts prior to electrophoresis thus allowing simplified analysis of those constituents which are labelled by the donating crosslinker.

SUMMARY OF THE INVENTION

We have developed a cleavable heterobifunctional, radioactively labelled, chemical crosslinking reagent for studying the interactions of proteins in situ. In our preferred embodiment one end of our crosslinker is photoactivatable. When reacted in the dark with proteins it forms covalent derivatives which can be purified and reconstituted into biological systems. These derivatives will form crosslinks to neighboring macromolecules only upon photolysis; reduction cleaves the crosslink and transfers the radiolabel to the second molecule, which can then be identified. The crosslinker gives the proper chemical behavior under biological conditions, reacts with high yield and with a very low level of nonspecific crosslinking, and can be used to identify protein-protein and other interactions at the cell surface and elsewhere.

Our crosslinker comprises (a) a functional group at one end capable of forming covalent bonds with a protein prior to introduction in situ; (b) a second functional group at the other end which will react with a second protein in situ upon photolysis or a similiar mechanism; (c) a cleavable bond which can be broken by reduction or comparable means; and (d) a label, preferably a radio-label, which is so situated such that upon cleavage, the label will remain with the second protein.

The functional groups capable of forming covalent bonds with proteins prior to introduction in situ may take various forms. We have used succinimide esters as functional groups for this purpose. These esters readily react with amino groups on proteins under mild conditions to form covalent derivatives. Other functional groups reactive with amino groups, sulfhydryl groups, phenolic or aliphatic hydroxyl groups, or other groups on the protein of interest could be used in particular applications.

The other end of our crosslinker employs a photosensitive functional group, such as a phenyl azide, which forms a reactive nitrene, to bind the crosslinker in situ. Other alkyl or aryl azides could be used in particular applications.

The cleavage mechanism in our crosslinkers is a disulfide link which is employed because it permits simple radio-labelling and is easily cleaved by reduction. Cis glycol links or other cleavable groups could be used in other applications.

The donation of a label to the in situ bound proteins can be achieved by introducing a radioisotope into the crosslinker during the synthesis of the photosensitive end. In our preferred embodiment, a radioisotope of sulfur, $^{35}S$ is used to form one-half of the disulfide link.

Upon cleavage the in situ bound protein is left with the labelled part of the broken disulfide link.

BRIEF DESCRIPTION OF THE DRAWING

FIG. 1 is a schematic drawing of a crosslinking scheme using our reagent.

DETAILED DESCRIPTION OF THE PREFERRED EMBODIMENT

Our invention is described in connection with the non-limiting example below.

EXAMPLE

The following diagram shows the four step synthesis of our crosslinking reagent:

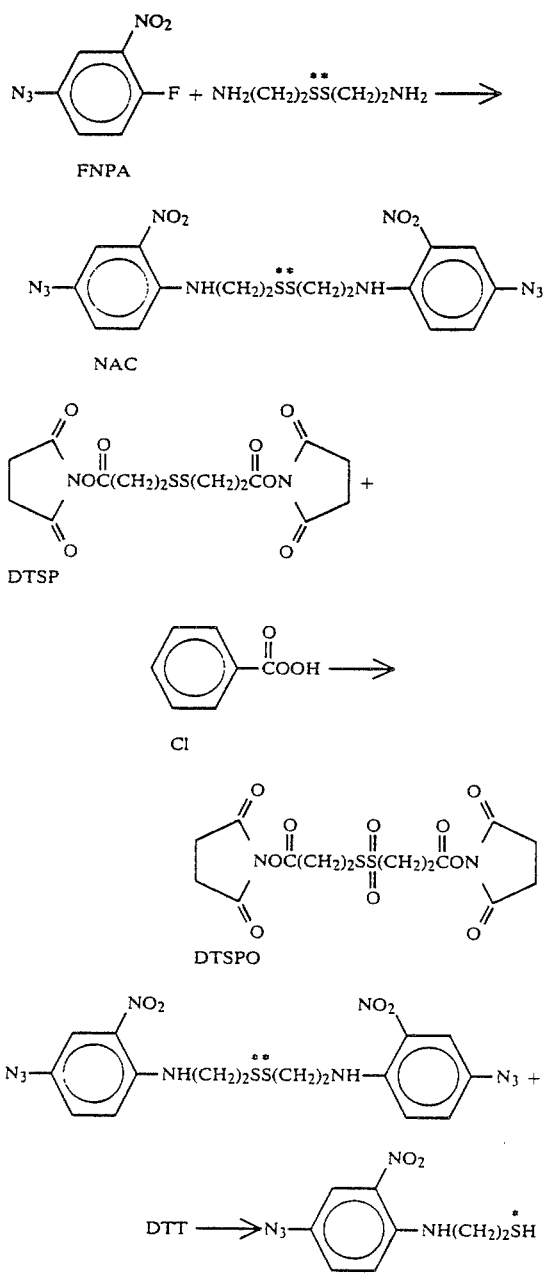

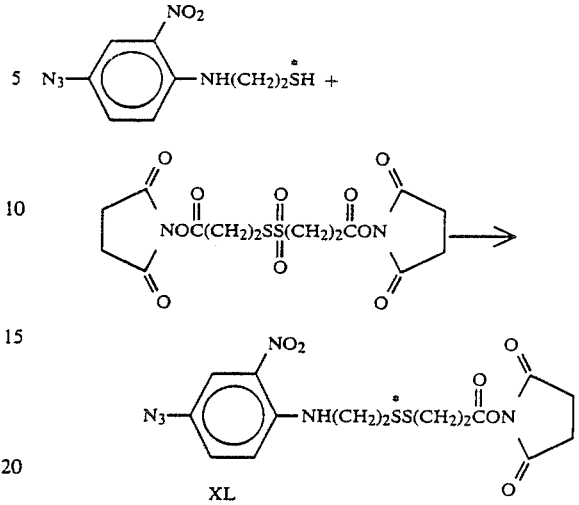

In step 1 bis-N-(2-nitro-4-azidophenyl)-cystamine (NAC) was prepared from 10.0 mCi[$^{35}$S]-labelled cystamine (New England Nuclear) at 250 mCi/mmol (40.0 μmol) dissolved in 0.30 ml methanol, with 40 mg 4-fluoro-3-nitro-phenylazide (FNPA) (215 μmol) and 25 μl triethylamine. After 48 hrs. in the dark at 35°, the dark red precipitate was collected by centrifugation, washed with methanol, and used immediately. The precipitate contained one main product (>90%) which co-migrated with cold NAC by thin layer chromatography on silica gel with ethylacetate and with benzene. Yield: 71% by radioactivity.

In step 2 Dithio-bis-(succinimidyl propionate)-S,S-dioxide (DTSPO) was prepared by adding 0.91 g 85% m-chloroperoxybenzoic acid (in 50 ml chloroform) dropwise over an hour into a solution of 0.97 g dithio-bis-(succinimidyl propionate) (DTSP) in 350 ml chloroform. The reaction was stirred for 4 hrs. on ice, then 1 hr. at room temperature. The solvent was removed by rotary evaporation, and the residue washed with benzene. The crude product was extracted with 60 ml dioxane and precipitated with a minimum amount of hexane. Yield: 0.40 g (40%). The product migrated as a single spot on thin layer chromatography in two solvent systems. Rf in methylene chloride:acetone:formic acid 100:25:1 =0.30; Rf in ethylacetate = 0.50. IR peaks characteristic of the succinimide ester appeared at 1810, 1780 and 1680 cm$^{-1}$.

In steps 3 and 4 reactions were kept in the dark as much as possible, and all manipulations were carried out in dim light. In step 3 6.9 mg dithiothreitol (DTT) (43 μmol) and 10 μl triethylamine were added to 7.05 mCi NAC at 250 mCi/mmol (28 μmol) in 1.0 ml chloroform, and in the final step, after 1 hr. at room temperature, 40 mg DTSPO (91 μmol) was added. The reaction was stirred for 20 min. during which time all the DTSPO dissolved. The solvent was evaporated under a stream of nitrogen and the residue extracted with 2 ml toluene. This solution was applied to a 5×0.7 cm silicic acid column packed in toluene, and the column was washed with toluene to elute unreacted NAC. The product 3-[(2-nitro-4-azidophenyl)-2-aminoethyl dithio]-N-succinimidyl propionate (XL) was eluted with chloroform which had been bubbled with nitrogen. The solvent was evaporated under a stream of nitrogen, the product was dissolved in toluene, centrifuged at 12000 g× 10 min. to remove silica fines, and stored in the dark under nitrogen at −20°. The product undergoes negligible decomposition under these conditions for 2-3 weeks, and continues to give good biochemical results for 6 weeks. XL migrated as a single spot on thin layer chromatography in two solvent systems. Rf in benzene=0.06; Rf in ethylacetate=0.77.

In FIG. 1, one use for our crosslinking reagent is shown schematically. In the first stage the succinimide ester moiety on the crosslinking reagent reacts with amino groups on proteins to form an amide linkage. S* denotes the radiolabelled sulfur. $^{35}$S label allows determination of the number of crosslinkers per molecule of protein. In stage two the labelled protein ($P_1$) is reconstituted with other proteins, cells, etc. In general, there will be interacting proteins ($P_2$) and noninteracting proteins ($P_3$). In stage 3, which can be at any time before photolysis, reduction cleaves the disulfide link to remove the radiolabelled sulfur. No proteins should remain labelled. In the fourth stage photolysis converts the azide group to a highly-reactive nitrene. In the fifth stage nitrene reacts at a second site to form a covalent bond. In general, this may take the form of self-reactions (a), specific crosslinking (b), nonspecific crosslinking (c), or abortive reaction with solvent (d). If samples are analyzed at this point without reduction, radiolabel will be found both in the starting protein $P_1$, and in various higher molecular weight complexes. In the sixth step reduction cleaves the disulfide link so that the radiolabel is associated with the second reaction site. The reaction products lead to self-labelling (a), specific labelling of proteins which interact with $P_1$ (b), and nonspecific labelling of proteins which are nearby but do not directly interact with $P_1$ (c). Our results show that nonspecific labelling (c) is very low whereas specific labelling (b) is readily detected.

We have used our crosslinker in the analysis of protein-protein interactions involving the glycoprotein, fibronectin. This protein is a major constituent of connective tissue in vivo, and is involved in the adhesion of cells to substrata in cell culture. Immunofluorescence and electron microscopic studies show that fibronectin forms extracellular fibrils whose arrangement is related to that of the microfilament system inside the cells.

To determine if the crosslinking reagent behaves as predicted in the presence of proteins, we studied its behavior in a simple model system. Gelatin coupled to Sepharose CL-4B binds fibronectin with high efficiency and a defined stoichiometry. This provides a convenient means for determining the location of the radiolabel after photolysis and reduction.

In one of our experiments our crosslinker (XL) was first bound to gelatin. Next we crosslinked gelatin to fibronectin on NIL8 fibroblasts. These cells were incubated with gelatin-XL in the dark, washed to remove unbound gelatin, photolyzed and reduced. The cells were lysed in 2% SDS containing ethylmercury phosphate to block disulfide exchange and run on SDS-PAGE.

Gel electrophoresis showed that after photolysis and reduction, only a single new protein with the molecular weight of fibronectin became labelled. Therefore, in this biological system, there was specific crosslinking of gelatin to fibronectin in the absence of any detectable non-specific crosslinking. An inhibitor of disulfide interchange during the binding and crosslinking states was not necessary, presumably because few sulfhydryls were present outside the cells. Therefore, the crosslinking reagent can be used to crosslink cell surface molecules under physiological conditions. Since our reagent does not require any particular functional groups to be present in the neighboring molecules, lipids, carbohydrates or nucleic acids, as well as proteins can be crosslinked. Our reagent and methods should also be useful for identifying virus receptors, antigen and hormone receptors, actin or tubulin binding proteins and for many other problems of this sort.

What we claim is:

1. A crosslinking reagent comprising;
   (a) a first functional group capable of forming a covalent derivative with a material of interest;
   (b) a second functional group capable of forming an in situ bond to a neighboring material upon photolysis,
   (c) a chemically cleavable bond separating said first and second groups; and
   (d) label means for labelling the neighboring material after cleavage of said bond, whereby in situ protein interactions can be studied.

2. The reagent of claim 1 wherein said first functional group is an ester.

3. The reagent of claim 2 wherein said ester is a succinimide ester.

4. The reagent of claim 1 wherein said second functional group is a group capable of forming a reactive nitrene upon photolysis.

5. The reagent of claim 4 wherein the second functional group is at least one member of the group of alkylazides, arylazides and aralkylazides.

6. The reagent of claim 5 wherein the second functional group is a phenylazide.

7. The reagent of claim 1 wherein the cleavable bond is a disulfide bond.

8. The reagent of claim 1 wherein the label means is a radioactive marker which remains with the second functional group upon cleavage.

9. The reagent of claim 1, 2, 3, 4, 5 or 6 wherein the cleavable bond is a disulfide bond and the label means is a radioisotope of sulfur which remains with the second functional group upon cleavage.

10. A reagent having the following formula:

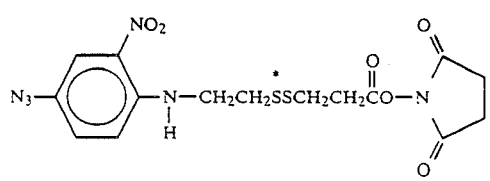

where S is a radioisotope of sulfur.

11. A method of analyzing interactions between biological materials in situ, the method comprising:
   (a) binding the first functional group of the cross-linking reagent of claim 1 to a material of interest in vitro;
   (b) introducing the crosslinking reagent and the bound material of interest into a study situs;
   (c) exposing the situs to light to activate the second functional group and the reagent and bind neighboring materials to the crosslinking reagent;
   (d) lysing the situs;
   (e) reducing the reagent;
   (f) isolating the labelled materials; and
   (g) analyzing the reduced, isolated materials for chemical composition.

* * * * *